United States Patent [19]

Jones

[11] Patent Number: 4,658,813
[45] Date of Patent: Apr. 21, 1987

[54] SUCTION HEAD HOLDER FOR A TRACHEOSTOMY TUBE

[76] Inventor: Hedwig E. Jones, 3519 Gemini Ct., Concord, Calif. 94519

[21] Appl. No.: 842,910

[22] Filed: Mar. 24, 1986

[51] Int. Cl.$^4$ .............................................. A61M 16/00
[52] U.S. Cl. ...................... 128/207.14; 128/DIG. 26; 248/230; 248/231.8; 604/174
[58] Field of Search .......................... 604/73, 179–180; 128/DIG. 26, 207.17, 207.14; 248/230, 231.8

[56] References Cited

U.S. PATENT DOCUMENTS

| | | | |
|---|---|---|---|
| 2,839,201 | 6/1958 | Auster | 248/231.8 X |
| 4,193,572 | 3/1980 | Horiuchi et al. | 248/231.8 X |
| 4,331,143 | 5/1986 | Foster | 128/DIG. 26 |
| 4,576,589 | 3/1986 | Kraus et al. | 128/DIG. 26 |

*Primary Examiner*—Stephen C. Pellegrino

[57] ABSTRACT

A device that allows a suction head to be clamped to a tracheostomy tube and left in place to dispose of secretions on a continuous basis by suction, without interfering with respirations or oxygenation. This is achieved by slipping a ring around the outer end of the tracheostomy tube bearing a holder for a glass suction head which comes to rest on the outer rim of the cannula, but does not extend inside the cannula. When connected to suction, mucus will be disposed of as it is coughed up, without causing the many problems of tracheostomy care.

3 Claims, 5 Drawing Figures

SUCTION HEAD HOLDER FOR A TRACHEOSTOMY TUBE

BACKGROUND OF THE INVENTION

1. Field of the Invention

The invention relates generally to a device that enables a suction head to be clamped onto a tracheostome tube. The suction head is connected by tubing to a suction machine and thus disposes of tracheal secretions as they are coughed up.

2. Description of the Prior Art

Tracheal secretions of patients that have tracheostomy tubes are disposed of in two ways:

(a) by deep suctioning that removes deep seated mucus; and (b) by superficial suctioning of mucus that is already coughed up.

Deep suctioning is done by introducing a suction catheter through the tracheostomy tube several inches into the trachea. The suction machine to which the suction catheter is connected then sucks out the deep seated mucus. This procedure requires sterile technique, is time consuming and can cause irritation of the tracheal walls. It is therefore desirable that it be kept to a minimum.

Superficial suctioning is done as required by using a glass suction head held to the opening of the tracheostomy tube. This is connected to a suction machine which sucks up mucus that is already coughed out and clogs the opening of the tracheostomy tube. However, it is difficult to anticipate a coughing spell, and it is not possible for nurses to spend sufficient time with anyone patient to immediately remove coughed up secretions. As a result tracheostomy care is unpleasant, time consuming, and hazardous. Large blobs of mucus are often found not only on the protective gauze dressing which surrounds the tracheostomy tube, but also on the patient's clothing and his oxygen collar when in use. Wet tracheostomy dressings have to be changed frequently, clothing must be changed and oxygen equipment cleaned of mucus, an unpleasant task at best. The skin surrounding the tracheostomy site is kept moist from the wet dressings and is thus more subject to yeast infections. The coughed-out mucus itself can also spread airborne infections.

This invention offers a way to dispose of secretions safely and effectively as they are coughed up and thereby eliminates the worst aspects of tracheostomy care.

SUMMARY OF THE INVENTION

The invention relates to a device that allows a suction head to be clamped to a tracheostomy tube, so that secretions can be disposed of by suction as they are coughed up. It consists of a wide, slightly flexible, open ring of plastic, or metal, or any other suitable material, that can be removably snapped onto, or slipped over, the outer end of a tracheostomy tube in such a way, that the suction head holder which it bears comes to rest on the outer rim of the tracheostomy cannula. A glass suction head is then slipped into the holder and connected by tubing to a suction machine. If at any time the patient is ambulatory, or suctioning is not practical for other reasons, this device can be removed to be used again as necessary.

It is an object of the invention to make tracheostomy care less unpleasant and time-consuming for nurses and patients and to minimize resultant infections.

DESCRIPTION OF THE PREFERRED EMBODIMENT

Figure 1:
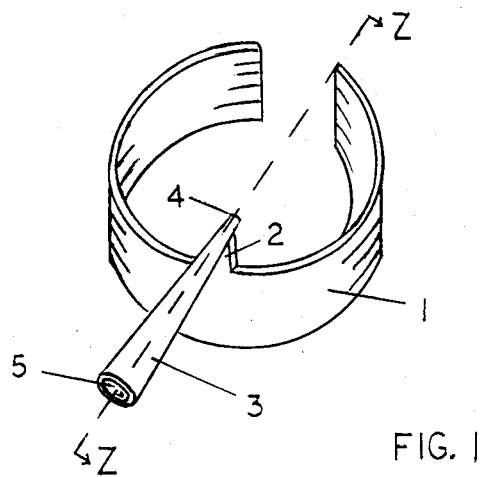
FIG. 1 is an enlarged elevational view of the suction head holder.
Figure 2:
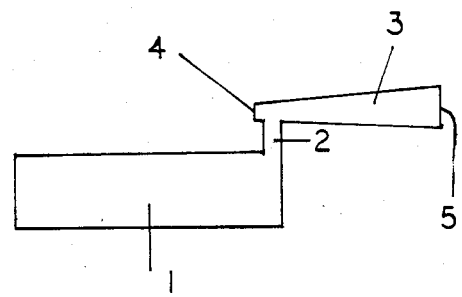
FIG. 2 is a sectional view of FIG. 1 along the line Z—Z.

Referring to FIGS. 1 and 2, an embodiment of the suction head holder is shown. In this embodiment an open-ended, wide ring or band 1 of a rigid, yet somewhat flexible material, like plastic or metal, is provided. The center of the band opposite the open end bears a short connecting member 2 which extends upward from it and is integrally bonded with it. Superposed on the connecting member 2 and at right angles to it and the ring is a hollow tube 3 with a proximal open end 4 and a distal open end 5. The tube 3 is bonded close to it's proximal end 4 to the connecting member 2. Both tube 3 and connecting member 2 should be rigid. The proximal end 4 of the hollow tube 3 extends slightly beyond the connecting member 2, the distance being equal to the thickness of the wall of a tracheostomy tube, and points towards the center of the ring 1. The tube 3 widens towards the distal end 5 and points away from the ring, giving access to suctioning when the device is in place.

Figure 3:
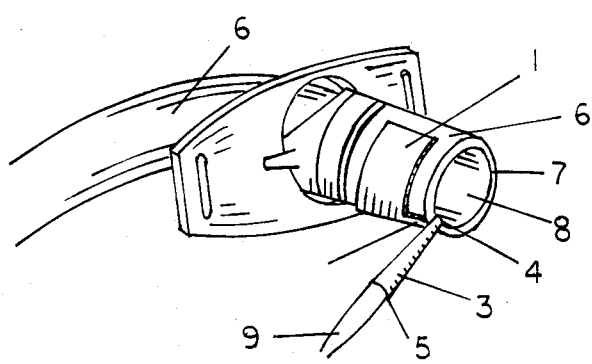
FIG. 3 is a view of a suction head holder in place on an adult sized tracheostomy tube with a glass suction head in place.

Referring to FIG. 3, an embodiment of the suction head holder is shown in place on an adult size tracheostomy tube 6. When in place, the ring 1 is firmly clamped around the outer end of the tracheostomy tube. The connecting member 2 rests against the outer wall of the tracheostomy tube 6 and it's longitudinal direction. The proximal end 4 of the hollow tube 3 forming the holder rests on the outer rim 7 of the tracheostomy tube 6, the end flush with the inner wall 8 of the tracheostomy cannula 6. The distal end 5 receives the glass suction head 9 which is connected by tubing to a suction machine. Coughed up mucus will pass by the proximal end 4 of the suction head holder and is disposed of by suction. As long as the proximal end 4 of the suction head holder does not extend into the tracheostomy cannula itself, but ends at it's inner wall 8, the suction will not interfere with the patient's respirations or oxygenation and there will still be access for deep suctioning if required.

Figure 4:
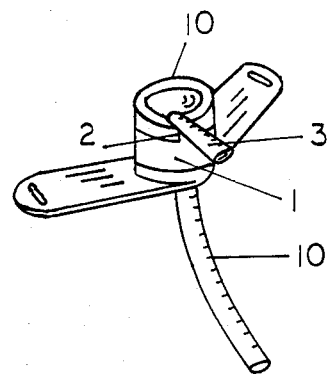
FIG. 4 is a view of a suction head holder in place on a pediatric sized tracheostomy tube.

Referring to FIG. 4, an embodiment of the invention is shown in place on a pediatric tracheostomy tube 10. The suction head holder will work in the same way, and can be made in sizes to fit various tracheostomy tubes.

Figure 5:
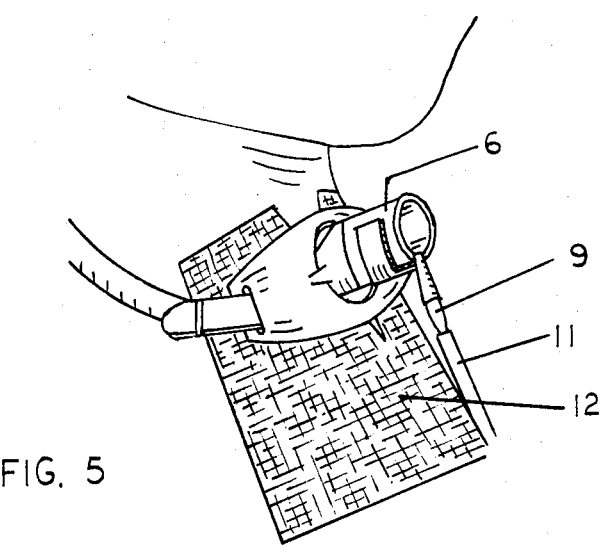
FIG. 5 is a view of a suction head holder in place on an inserted tracheostomy tube with suction connected.

Referring to FIG. 5, an embodiment of the invention is shown in place on an inserted tracheostomy tube. Suction tube 11 is attached. The protective gauze dressing 12 that surrounds the tube 6 will be kept dry and clean, shielding the ostomy site underneath it from infection.

A further advantage of this embodiment allows the ring to be moved around the tracheostomy tube so that access to suctioning can be effected from either side of the patient or any direction that is convenient.

Although embodiments of the invention are illustrated in the drawings and are previously described in detail, this invention encompasses any design and relationship of components which will function in a similar manner and which will provide the equivalent result. For example, the invention could be manufactured and marketed together with suitable glass suction heads.

I claim:

1. A suction head holder for a tracheostomy tube, comprising:
    (a) a wide, open, snap-on ring of a resilient material, that will firmly engage the protruding end of an inserted tracheostomy tube;
    (b) a connecting member bonded to the ring and extending upwards from it and providing rigid mechanical support for a holder;
    (c) a holder for a glass suction head in the shape of a hollow tube with an open proximal end and an open distal end, which is integrally bonded to the connecting member in such a way that, when in use, the proximal end of the holder will come to rest on top of the outer rim of the tracheostomy tube and will be flush with it's inner wall.

2. A suction head holder as recited in claim 1, in which the hollow tube that forms the holder widens gradually towards the distal end to take the shape of, and provide access for, a glass suction head.

3. A suction head holder as recited in claim 2, in which the holder is rigid and of a sufficient length to hold the suction head firmly in place and always at the same angle.

* * * * *